United States Patent [19]

Prybeck

[11] 3,958,750

[45] May 25, 1976

[54] TRANSPARENT MEDICINE DISPENSER WITH HOSPITAL MEDICINE CARD

[75] Inventor: Mary Prybeck, Fords, N.J.

[73] Assignee: Lawrence Peska Associates, Inc., New York, N.Y. ; a part interest

[22] Filed: Nov. 21, 1974

[21] Appl. No.: 525,889

[52] U.S. Cl. .................................... 229/56; 150/7; 206/260; 229/62

[51] Int. Cl.$^2$ .................................... B65D 31/12

[58] Field of Search .................. 229/72, 56, 62, 76, 229/77, 82, DIG. 3, 80; 150/7, 3; 206/260

[56] References Cited

UNITED STATES PATENTS

| | | | |
|---|---|---|---|
| 200,853 | 3/1878 | Benham | 229/72 |
| 927,339 | 7/1909 | Earle | 229/72 |
| 1,111,981 | 9/1914 | Walker, Jr. | 229/72 X |
| 2,037,839 | 4/1936 | Wagenseller | 229/DIG. 3 X |
| 2,217,949 | 10/1940 | Heywood | 229/80 X |
| 2,329,444 | 9/1943 | Snyder | 229/62 |
| 2,718,105 | 9/1955 | Ferguson et al. | 229/53 X |
| 3,557,853 | 1/1971 | Jones | 150/7 |

FOREIGN PATENTS OR APPLICATIONS

| | | | |
|---|---|---|---|
| 1,523,206 | 5/1968 | France | 150/3 |
| 213,865 | 4/1924 | United Kingdom | 206/260 |

*Primary Examiner*—William Price
*Assistant Examiner*—Stephen P. Garbe
*Attorney, Agent, or Firm*—Jack D. Slobod

[57] ABSTRACT

Disclosed is a package formed of three sheets of polyolefin plastic with an open envelope on one side for a hospital medicine card and a closure-equipped flap on the other side for a pouch holding pills. A hypodermic syringe containing an injection can be carried under the flap by using the closure means placed closer to the fold of the flap.

1 Claim, 5 Drawing Figures

34

14

12

28

26

30

18

32

16

24

TRANSPARENT MEDICINE DISPENSER WITH HOSPITAL MEDICINE CARD

BACKGROUND OF THE INVENTION

1. Field of the Invention

This invention relates generally to transparent plastic packages for dispensing medication according to instructions appearing on a card carried by the package.

With the ever increasing shortage of nurses, it is critical to save the time of the nurses on duty so they may look after more patients. One way this can be done is to have the prescribing physician write instructions on cards bearing the name of the patient. This practice also encourages the use of less experienced staff such as orderlies and nurse's aids in performing tasks previously reserved to nurses and this without risk of error.

2. Description of the Prior Art

The art to which this invention relates already is aware, inter alia, of the following U.S. Pat. Nos: 3,685,720; 3,460,742; 2,652,149; and 3,761,013. The complex packages described in the foregoing patents either contain a memo pad or are intended to hold instruments during sterilization with steam or ethylene oxide.

SUMMARY OF THE INVENTION

The principal object of this invention is to provide an article of this character which combines simplicity, strength and durability in a high degree, together with inexpensiveness of construction.

Other objects of this invention will in part be obvious and in part hereinafter pointed out.

The invention accordingly consists in the features of construction, combinations of elements, and arrangement of parts which will be exemplified in the construction hereinafter described, and of which the scope of application will be indicated in the following claims.

In the accompanying drawing, in which is shown one of the various possible illustrative embodiments of this invention, wherein like reference character identify the same or like parts:

Figure 1:
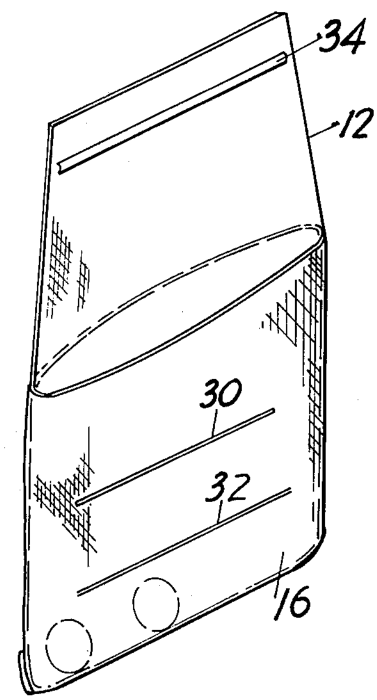
FIG. 1 is a perspective view of a package embodying the features of the invention shown with its closure flap open.

With reference to the drawing, there is shown and illustrated a package constructed in accordance with the principles of the invention and designated generally by reference character 10.

Figure 4:
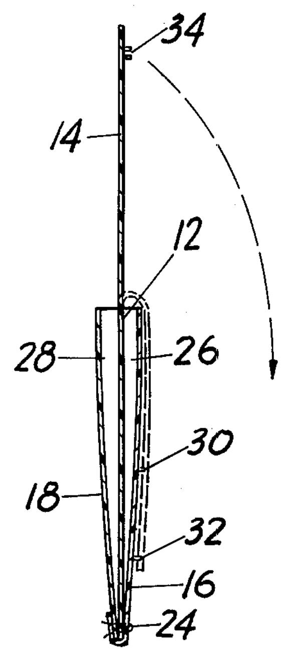
FIG. 4 is a side view of the package.

As shown in FIGS. 1 and 4, the package 10 comprises three plies of heat-sealable plastic such as polyethylene, polypropylene or other pliable and transparent material. The center member 12 terminates in an elongated closure flap 14. Center member 12 has on each side thereof a plastic member of the same width but lesser height 16 and 18. The three members are secured by heat sealing or otherwise along two sides and bottom thereof along 20, 22 and 24. Alternatively, center member 12 can be cut long enough to form one of the side members 16 or 18 after folding. Two envelopes or pouches 26 and 28 are thus formed with pouch (26) adapted to be closed by flap 14, as shown in FIG. 4.

Figure 3:
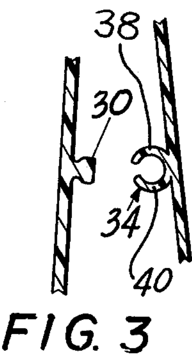
FIG. 3 is a detailed view of the flap closure.
Figure 2:
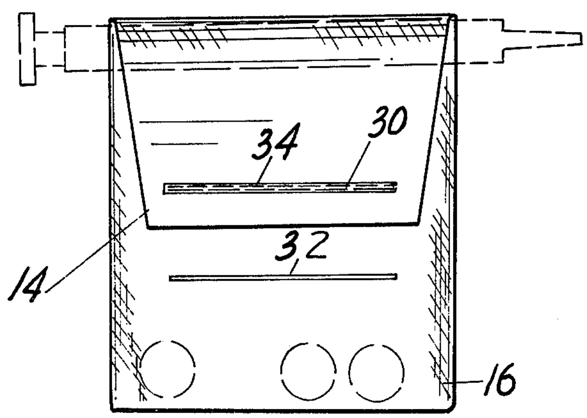
FIG. 2 is a front elevational view of the same with a syringe carried under the closed flap.
Figure 5:
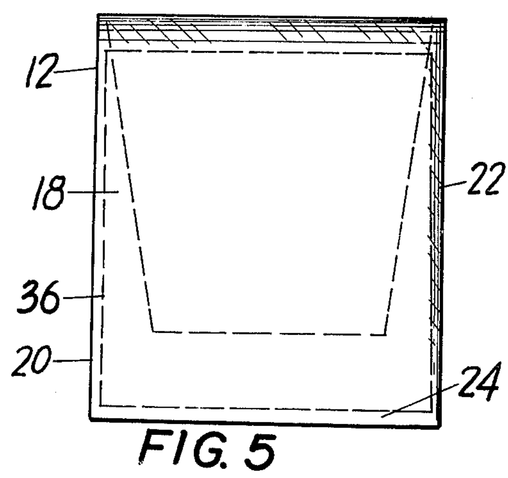
FIG. 5 is a back view of the package.

FIG. 3 shows the closure contact adhesive means used to close pouch 26. These are commercially available as zip locks such as used on shopping bags and consist of adhesive strips carrying interlocking elongated hook 30 and eye 34 members or as "velcro" bands. A pair of spaced hook members or blades having bulbous ends 30 and 32 are mounted on the front of member 16. The eye member 34 is mounted on the underside of flap 14 and is formed by a pair of opposed elongated arcuate blades 38 and 40 for selectively frictionally engaging either of blades 30 and 32 therebetween. As a result, there is formed an adjustable closure with either member 30 or 32; the former being used when the flap carries an item such as the syringe shown in FIG. 2.

Pouch 26 is designed to hold pills or capsules or the like at which time it is closed by pressing elements 34 and 32.

Pouch 28 is intended to carry a hospital medicine card 36 carrying data such as:

room and bed number
name of patient
name of medication
time and frequency of administration
date treatment started
date treatment ended
remarks
name of prescribing physician Since both sides of the card are visible through the package, the above data can be divided between the front and back of the card.

Where desired, the package of the invention can be sterilized in known fashion with steam or gases.

The package can conveniently have the following dimensions:

| | |
|---|---|
| height of sides | 3 inches |
| width of sides | 3⅛ inches |
| length of flap | 2½ inches |
| spacing between hooks 30 and 32 | ¾ inch |

The operation and use of the invention hereinabove described will be evident to those skilled in the art to which it relates from a consideration of the foregoing.

It will thus be seen that there is provided a device in which the several objects of this invention are achieved, and which is well adapted to meet the conditions of practical use.

As various possible embodiments might be made of the above invention, and as various changes might be made in the embodiment above set forth, it is to be understood that all matter herein set forth or shown in the accompanying drawing is to be interpreted as illustrative and not in a limiting sense.

With reference to what has been shown and described, I claim as new and desire to secure by Letters Patent:

1. A package for medication to be dispensed according to directions given on a card comprising: first and second back to back open pouches formed by three layers of transparent flexible plastic sheets adhered along three sides thereof, a center one of said sheets being common to said pouches and being extended beyond said pouches to form a flap for closing said first pouch; a pair of opposed elongated arcuate blades projecting integrally from one side of said flap facing said first pouch; and a plurality of spaced apart elongated bulbous blades projecting integrally from the front of said first pouch, each of said bulbous blades being configured for frictional engagement between said arcuate blades whereby said first pouch is adjustably closeable to accomodate articles of various thicknesses; said second pouch being adapted to hold said card therein.

* * * * *